United States Patent
Strohmaier et al.

(10) Patent No.: US 7,098,352 B2
(45) Date of Patent: Aug. 29, 2006

(54) CALCIUM SALT SAPONIFICATION OF POLYUNSATURATED OILS

(75) Inventors: George K. Strohmaier, Medina, OH (US); Nestor D. Luchini, Naperville, IL (US); Michael A. Varcho, Mentor, OH (US); Eiler D. Frederiksen, Henderson, NV (US)

(73) Assignee: Virtus Nutrition LLC, Fairlawn, OH (US)

( * ) Notice: Subject to any disclaimer, the term of this patent is extended or adjusted under 35 U.S.C. 154(b) by 0 days.

(21) Appl. No.: 10/716,292

(22) Filed: Nov. 18, 2003

(65) Prior Publication Data

US 2004/0158087 A1 Aug. 12, 2004

Related U.S. Application Data

(63) Continuation-in-part of application No. 10/229,337, filed on Nov. 18, 2002, now abandoned.

(60) Provisional application No. 60/334,471, filed on Nov. 16, 2001.

(51) Int. Cl.
*C07C 51/00* (2006.01)
(52) U.S. Cl. ...................... 554/156; 426/807
(58) Field of Classification Search ............... 554/156; 426/807
See application file for complete search history.

(56) References Cited

U.S. PATENT DOCUMENTS

| | | | |
|---|---|---|---|
| 3,959,493 A | 5/1976 | Baalsrud et al. |
| 4,298,730 A | 11/1981 | Galleymore et al. |
| 4,472,432 A | 9/1984 | Iwamura et al. |
| 4,495,201 A | 1/1985 | Bondar et al. |
| 4,642,317 A | 2/1987 | Palmquist et al. |
| 4,826,694 A | 5/1989 | McAskie |
| 4,853,233 A | 8/1989 | McAskie |
| 4,909,138 A | 3/1990 | McAskie |
| 5,043,328 A | 8/1991 | Weithmann |
| 5,143,737 A | 9/1992 | Richardson |
| 5,234,701 A | 8/1993 | Cummings et al. |
| 5,382,678 A | 1/1995 | Vinci et al. |
| 5,430,066 A | 7/1995 | Cook et al. |
| 5,456,927 A | 10/1995 | Vinci et al. |
| 5,541,225 A | 7/1996 | Leaf et al. |
| 5,554,646 A | 9/1996 | Cook et al. |
| 5,604,258 A | 2/1997 | Ferrante et al. |
| 5,618,558 A | 4/1997 | Horrobin et al. |
| 5,681,971 A | 10/1997 | Scheibel et al. |
| 5,763,484 A | 6/1998 | Horrobin |

(Continued)

FOREIGN PATENT DOCUMENTS

EP 0 387 023 A1 9/1990

(Continued)

OTHER PUBLICATIONS

Formo et al., "Soap," *Bailey's Industrial Oil and Fat Products*, 4th ed., vol. 1, pp. 511-529 (1979).

(Continued)

*Primary Examiner*—Deborah D. Carr
(74) *Attorney, Agent, or Firm*—Synnestvedt & Lechner LLP (57) ABSTRACT

Methods for the preparation of storage-stable fatty acid calcium salt products by forming a reactive admixture of (a) an unsaturated fatty acid glyceride feedstock; and (b) from about 10% to about 30% of the total admixture weight of calcium hydroxide; and heating the admixture to a temperature at which the fatty acid glycerides saponify to form fatty acid calcium salts in an atmosphere in which the partial pressure of oxygen has been reduced by an amount effective to provide an improvement in storage stability. Storage stable calcium salts of unsaturated fatty acids prepared by the inventive method are also disclosed.

46 Claims, 4 Drawing Sheets

U.S. PATENT DOCUMENTS

| | | |
|---|---|---|
| 5,767,156 A | 6/1998 | Ferrante et al. |
| 5,804,210 A | 9/1998 | Cook et al. |
| 5,814,663 A | 9/1998 | Cook et al. |
| 5,837,731 A | 11/1998 | Vaddadi |
| 5,859,055 A | 1/1999 | Horrobin et al. |
| 5,861,433 A | 1/1999 | Akimoto et al. |
| 5,888,541 A | 3/1999 | Horrobin et al. |
| 5,914,346 A | 6/1999 | Cook et al. |
| 5,968,792 A | 10/1999 | Wenzel et al. |
| 6,020,378 A | 2/2000 | Cook et al. |
| 6,034,132 A | 3/2000 | Remmereit |
| 6,229,031 B1 | 5/2001 | Strohmaier et al. |
| 6,559,324 B1 * | 5/2003 | Strohmaier et al. ......... 554/156 |
| 6,576,667 B1 | 6/2003 | Strohmaier et al. |
| 6,737,078 B1 | 5/2004 | Kelley ................. 424/442 |

FOREIGN PATENT DOCUMENTS

| | | |
|---|---|---|
| WO | WO 99/66877 | 12/1999 |

OTHER PUBLICATIONS

Formo et al., "Hydrolis," *Bailey's Industrial Oil and Fat Products*, 4th ed., vol. 1, pp. 100-103 (1979).

Formo et al., "Fat Splitting," *Bailey's Industrial Oil and Fat Products*, 4th ed., vol. 2, pp. 97-113 (1979).

* cited by examiner

CALCIUM SALT SAPONIFICATION OF POLYUNSATURATED OILS

CROSS-REFERENCE TO RELATED APPLICATIONS

The present application is a Continuation-In-Part of U.S. patent application Ser. No. 10/229,337 filed Nov. 18, 2002 now abandoned, which, in turn, claims priority benefit under 35 U.S.C. § 119(e) of U.S. Provisional Patent Application Ser. No. 60/334,471 filed Nov. 16, 2001. The disclosures of both applications are incorporated by reference.

BACKGROUND

The present invention relates to the preparation of unsaturated fatty acid calcium salt nutritional supplements from high glyceride content polyunsaturated oils, including fish oils. The present invention particularly relates to fatty acid calcium salts rich in desirable unsaturated fatty acids such as omega-3 fatty acids, including eicosapentaenoic acid (EPA), docosahexaenoic acid (DHA), decosopentaenoic acid (DPA) and linolenic acid (LNA).

A variety of unsaturated fatty acids have been identified as desirable for producing a diversity of nutritional and physiological benefits in humans and lower animals, including pets and livestock, and accordingly have attracted attention as nutritional supplements. Omega-3 fatty acids, for example, have been discovered to promote animal fertility, and have other nutritional and physiological properties as well. Conjugated Linoleic Acids (CLA's) have been discovered to possess a diverse and complex level of biological activity. Anti-carcinogenic properties have been well documented, as well as stimulation of the immune system. U.S. Pat. No. 5,914,346 discloses the use of CLA's to enhance natural killer lymphocyte function. U.S. Pat. No. 5,430,066 describes the effect of CLA's in preventing weight loss and anorexia by immune system stimulation.

CLA's have also been found to exert a profound generalized effect on body composition, in particular, upon redirecting the partitioning of fat and lean tissue mass. U.S. Pat. Nos. 5,554,646 and 6,020,378 disclose the use of CLA's for reducing body fat and increasing lean body mass. U.S. Pat. No. 5,814,663 discloses the use of CLA's to maintain an existing level of body fat or body weight in humans. U.S. Pat. No. 6,034,132 discloses the use of CLA's to reduce body weight and treat obesity in humans. CLA's are also disclosed by U.S. Pat. No. 5,804,210 to maintain or enhance bone mineral content.

It is also known that supplementing the diet of livestock with unsaturated fatty acids will alter the livestock fatty acid profile, so that, for example, feeding dairy cows and beef cattle a source of unsaturated fatty acids beneficial to humans will yield dairy and beef products for human consumption enriched with the beneficial unsaturated fatty acids. For example, U.S. Pat. No. 5,143,737 discloses that the unsaturated fat content of milk and meat from ruminant animals can be increased by incorporating the intended unsaturated fat into the diet of the ruminant.

Thus, meat and milk enriched with CLA's and other unsaturated fatty acids can be obtained by supplementing ruminant diets with unsaturated fatty acids such as CLA. Dairy cows and beef cattle fed a source of CLA not only will produce lower fat content dairy and beef products, the products will be enriched with CLA's as well. Dietary supplementation of dairy cows and beef cattle with unsaturated fatty acids beneficial to humans can also be used to displace and thereby reduce the levels of undesirable saturated fatty acids in dairy and beef products.

The beneficial effects produced by unsaturated fatty acids are not limited to CLA's. Other unsaturated fatty acids are disclosed to be useful for treating diabetes (U.S. Pat. No. 4,472,432), heart disease (U.S. Pat. Nos. 4,495,201; 5,541,225 and 5,859,055), prostaglandin deficiencies (U.S. Pat. No. 5,043,328), malaria (U.S. Pat. No. 5,604,258), osteoporosis (U.S. Pat. Nos. 5,618,558 and 5,888,541), cancer (U.S. Pat. No. 5,763,484), immune system function (U.S. Pat. No. 5,767,156), Huntington's Chorea (U.S. Pat. No. 5,837,731) and inflammation (U.S. Pat. No. 5,861,433). The disclosures of the foregoing patents are all incorporated by reference.

It has further been discovered that ruminants fed a source of trans-C18:1 fatty acids will have decreased concentrations of milk fat, hepatic triacylglycerol, and lower incidence of sub-clinical ketosis during early postpartum, and that feeding a source of linoleic (C18:2) fatty acids during the transition period will increase synthesis of $PGF_{2\alpha}$. The linoleic fatty acids thus hasten uterine involution and reduce the incidence of clinical and sub-clinical uterine inflammation; which translates to increased fertility.

Unsaturated fatty acids, however, undergo hydrogenation to more saturated and completely saturated fatty acids by microbial action in the rumen and must be fed to ruminants in a protected form. The aforementioned U.S. Pat. No. 5,143,737 discloses the encapsulation of unsaturated fatty acids with non-toxic organic materials to protect the unsaturated fatty acids from microbial action in the rumen. The most familiar form in which fatty acids in general are protected from microbial action in the rumen are the fatty acid calcium salts disclosed by U.S. Pat. Nos. 4,642,317; 4,826,694; 4,853,233 and 4,909,138. This form of fatty acid protection is widely accepted in the dairy and beef cattle industries.

Unsaturated fatty acids, however, do not readily react to form calcium salts using the processes disclosed by the above-listed patents. Instead of forming free-flowing granules, a mass develops that hardens into a tough material that resists grinding into the fine particles required for consumption by cattle. The resulting material also lacks storage stability. The product tends to auto-oxidize through an exothermic reaction that leads to a congealing of the product mass from its free flowing granular state to a hard amorphous state, suggesting that significant quantities of unreacted starting materials are present in the final product.

U.S. Pat. No. 6,559,324 discloses hydrolysis methods for the preparation of calcium salts of unsaturated fatty acids having 20 percent by weight glycerides. U.S. Pat. No. 6,576,667 discloses methods by which calcium salts of unsaturated fatty acids having as high as 60 percent by weight glycerides can be prepared. The disclosures of both patents are incorporated by reference. However, commercial sources of unsaturated fatty acids such as fish oils have glyceride contents as high as 100 percent by weight, which remain difficult to convert to storage stable free-flowing fatty acid calcium salts. U.S. Pat. No. 6,576,667 addresses this problem by diluting the high glyceride content oils to glyceride levels below 60 weight percent with lower glyceride content fatty acid feedstocks such as Palm Fatty Acid Distillates (PFAD's). However, this also reduces the unsaturated fatty acid concentration in the fatty acid calcium salt product, requiring greater quantities to be fed as part of a feed ration to adequately supplement the ruminant diet.

U.S. Pat. No. 6,229,031 discloses a saponification method by which calcium salts of fatty acids having as high as 100 percent by weight glycerides can be prepared. The disclosure of this patent is also incorporated by reference. However, calcium salts prepared from fatty acids with a significant degree of unsaturation have been discovered to lack storage stability.

A need exists for a method by which unsaturated fatty acid calcium salts having acceptable storage stability can be prepared.

SUMMARY OF THE INVENTION

This need is met by the present invention. It has now been discovered that improvements in the storage stability of saponified unsaturated fatty acid calcium salts can be significantly improved by performing the saponification method of U.S. Pat. No. 6,229,031 in an atmosphere in which the partial pressure of oxygen has been reduced. While it is known to exclude oxygen from a reaction process to prevent explosion or fire, or the oxidation of the ingredients and end product at elevated temperatures during the course of a reaction, what was unexpected is that minimizing atmospheric oxygen in the method of the present invention also improves the shelf life and storage stability of the finished product long after the reaction is completed.

The shelf life and storage stability of unsaturated fatty acid calcium salt products varies with unsaturated fatty acid content and degree of unsaturation. Shelf life decreases as polyunsaturated fatty acid content increases. Unsaturated fatty acid calcium salt products must possess sufficient shelf life and storage stability to pass without objection in the field. For purposes of the present invention, "shelf life" is defined as the time period required before product degradation exceeds levels considered acceptable to those of ordinary skill in the art. For a product to have adequate storage stability, the shelf life must exceed the amount of time the product would be expected to spend in storage after manufacture before being fed to a ruminant. Typically this is about six months.

Higher levels of mono-unsaturated fatty acids in glyceride sources are needed before a saponified calcium salt product will exhibit storage instability over a typical shelf life. Significantly lower quantities of polyunsaturated fatty acids, however, will reduce calcium product shelf life to unacceptable levels. At lower mono-unsaturated fatty acid concentrations the presence of polyunsaturated fatty acids will result in storage instability in an otherwise stable mono-unsaturated fatty acid calcium salt product with an adequate shelf life. Nevertheless, many fatty acid glyceride sources have mono- and polyunsaturated fatty acid levels that will produce a storage stable calcium salt product. Palm oil calcium salts, for example, possess adequate storage stability when prepared by the method of U.S. Pat. No. 6,229,031.

The method of the present invention is thus particularly useful when used to saponify fatty acid glycerides with levels of mono- and polyunsaturated fatty acids that would otherwise produce an unstable calcium salt product when saponified in the presence of oxygen. For purposes of the present invention, such fatty acid glycerides are referred to as "fatty acid feedstocks with an unsaturated fatty acid concentration sufficient to form unstable calcium salt products when saponified in an ambient atmosphere," and "unstable calcium salt products" are defined as calcium salt products with an inadequate "shelf life" as that term is defined in the present specification.

Therefore, according to one aspect of the present invention, a method for the preparation of a storage-stable fatty acid calcium salt product by:

forming a reactive admixture of (a) a unsaturated fatty acid glyceride feedstock; and (b) from about 10% to about 30% of the total admixture weight of calcium hydroxide; and heating the admixture to a temperature at which the fatty acid glycerides saponify to form fatty acid calcium salts in an atmosphere in which the partial pressure of oxygen has been reduced by an amount effective to provide an improvement in storage stability.

The partial pressure of oxygen in the reactive atmosphere may be reduced by inert gas blanketing of the admixture with, for example, nitrogen, carbon dioxide or argon, or by heating the admixture under vacuum. Nitrogen blanketing methods are preferred, as are methods in which atmospheric oxygen is essentially eliminated.

The saponification method of the present invention is typically applied to fatty acid glyceride feedstocks having greater than about 45% by weight of the fatty acid content in the form of fatty acid glycerides, and having an unsaturated fatty acid concentration sufficient to form unstable calcium salt products when saponified in an ambient atmosphere. The method can be used to prepare storage-stable products from unsaturated fatty acid sources such as fish oils having glyceride levels as high as 100% by weight.

According to another aspect of the present invention storage-stable unsaturated fatty acid calcium salt products are provided that are prepared by the method of the present invention. The present invention thus provides storage-stable calcium salts of unsaturated fatty acids beneficial to humans or livestock from feedstocks for those acids that are typically very high in glyceride content, without having to significantly dilute the feedstock, if at all, with low glyceride content feedstocks that contain little, if any, of the beneficial unsaturated fatty acids. Thus, essentially any unsaturated oil containing useful levels of beneficial unsaturated fatty acids is suitable for use with the present invention, and for purposes of the present invention is included within the definition of an unsaturated oil.

The present invention can be used with unsaturated oils having what was until now considered a low level of beneficial unsaturated fatty acids among the total unsaturated fat content, because with the present invention there is no need to dilute the feedstock with saturated fatty acids and the unsaturated fatty acid concentration is essentially conserved over time. Storage-stable calcium salts of unsaturated oils containing between about 3 and about 100 weight percent unsaturated fatty acids based on the total fatty acid content can be formed using the methods of the present invention. Oils with lower levels of beneficial unsaturated fatty acids may be used if they have utility based on their beneficial unsaturated fatty acid content.

Among the beneficial unsaturated fatty acids, beneficial polyunsaturated fatty acids are particularly preferred, and especially omega-3 such as EPA, DHA, DPA and LNA, and omega-6 fatty acids such as linoleic acid, CLA's and arachidonic acid, because of their reproductive and other benefits. Oils which are a high glyceride content source of omega-3 and omega-6 fatty acids, such as fish oils, may be directly saponified by the method of the present invention to form storage-stable calcium salt products without first diluting the oil with saturated fatty acids. The resulting products contains storage-stable levels of omega-3 and omega-6 fatty acid calcium salts that heretofore could not be attained using prior art methods.

Therefore, according to yet another aspect of the present invention a free-flowing storage-stable fatty acid calcium salt product is provided containing at least one unsaturated fatty acid, wherein the total unsaturated fatty acid content is between about 40 and about 95% by weight. Preferred products contain beneficial polyunsaturated fatty acids such as omega-3 and omega-6 fatty acids, with a product containing at least one polyunsaturated fatty acid selected from DHA, EPA, DPA, LNA, linoleic and arachidonic acid, each at a level between about 1 and up to about 80% by weight being particularly preferred. Conjugated polyunsaturated fatty acids such as CLA's are also preferred.

The foregoing and other objects, features and advantages of the present invention are more readily apparent from the detailed description of the preferred embodiments set forth below, taken in conjunction with the accompanying drawings.

DETAILED DESCRIPTION OF PREFERRED EMBODIMENTS

The present invention provides a process by which unsaturated fish, animal and vegetable fats, oils and other unsaturated fatty acid glyceride content materials, such as acid oils and acidulated soap stocks, may be converted to a storage-stable free-flowing powder or granular fatty acid calcium salts having utility as nutritional supplements in general and as rumen bypass feed supplements in particular. The term "glyceride" as employed herein includes $C_{10}$–$C_{22}$ fatty acid monoglycerides, diglycerides and triglycerides, and any mixture thereof.

Typical fatty acid glyceride feedstocks range in fatty acid content between $C_{10}$ and $C_{22}$ fatty acids and fatty acid glycerides. The economic advantages provided by the process of the present invention are obtained when using fatty acid glyceride feedstocks having glyceride concentrations that form unsuitable calcium salt products by hydrolysis methods, and unsaturated fatty acid concentrations sufficient to form unstable calcium salt products when saponified in an ambient atmosphere. Usually, fatty acid glyceride feedstocks cannot be hydrolyzed to form suitable calcium salts at glyceride contents of about 45% by weight and greater. However, the method of the present invention can be employed with fatty acid glyceride feedstocks in which from about 15% to about 100% by weight of the fatty acids are in glyceride form. The method of the present invention will also form calcium salts using lower glyceride content fatty acid glyceride feedstocks, and with glyceride-free fatty acid feedstocks.

The method of the present invention will improve the storage stability of essentially any saponified unsaturated fatty acid calcium salt product, and, in particular, polyunsaturated fatty acid calcium salt products, even those considered by the ordinarily skilled artisan to be adequately storage stable. Thus, the process of the present invention can be used to prepare fatty acid calcium salts from unsaturated oils of animal, vegetable or fish origin, including those disclosed in the above-referenced U.S. Pat. No. 6,576,667. Examples of suitable vegetable oils include soybean oil, cottonseed oil, flax seed oil, rape seed oil, and byproducts thereof, and oils derived from marine vegetation such as algae, kelp, and byproducts thereof. Examples of fish oil sources include menhaden, herring, mackerel, caplin, tilapia, tuna, sardine, pacific saury, krill, salmon, anchovy, and byproducts thereof. Examples of oil byproducts include acid oils and acidulated soap stocks.

Such fatty acid glyceride feedstocks typically contain from about 10 to about 100 weight % of the fatty acid content in the form of fatty acid glycerides, from about 0 to about 90% by weight of free fatty acids, and less than 5% by weight of moisture, insolubles and unsaponifiables. The feedstocks also typically contain from about 40 to about 95% by weight, and preferably between about 60 and about 80% by weight, of total unsaturated fatty acids, with between about 30 and about 80% by weight of the total being polyunsaturated. The method of the present invention thus provides storage stable fatty acid calcium salts containing between about 30 and about 80% by weight of one or more unsaturated fatty acids based on total product weight, of which between about 20 and about 70% by weight are one or more polyunsaturated fatty acids. The calcium salts contain less than 5% by weight, and preferably less than 1% by weight of unreacted glycerides. Other conventional biologically active ingredients can be added to the calcium salt products at conventional levels by known means.

While the calcium salts of the present invention can be used as rumen-inert feed supplements for ruminants such as cattle, the unsaturated fatty acid calcium salts are also useful in general as a nutritional supplement for humans and other mammals, including pets such as dogs and cats, and non-mammals, including birds and fishes, when formulated to contain unsaturated fatty acids beneficial to the respective species. The beneficial unsaturated fatty acid calcium salt nutritional supplements can also be fed to livestock to produce meat, poultry and dairy products enriched with the beneficial unsaturated fatty acids for consumption by species for which the unsaturated fatty acids are beneficial.

Examples of specific unsaturated fatty acids that are beneficial to humans, livestock, pets, birds or fishes, and which can be converted by the saponification method of the present invention to storage-stable fatty acid calcium salts, include linoleic acid (C18:2), arachidonic acid (C20:4) and the isomers thereof, omega-3 fatty acids such as DHA, EPA, DPA, LNA, and the like, omega-6 fatty acids, CLA isomers having utility as human dietary supplements, including the 10,12 and 9,11 isomers, specific examples of which include the trans 10, trans 12; trans 10, cis 12; cis 10, trans 12; cis 10, cis 12; trans 9, trans 11; trans 9, cris 9, trans 11 and cis 9, cis 11 isomers, trans fatty acids isomers having utility as dietary supplements for livestock, including C18:1 isomers such as trans-9-octadecenoic acid. A particularly preferred product contains at least one polyunsaturated fatty acid selected from, about 1 to about 25% by weight DHA, about 1 to about 25% by weight EPA, about 1 to about 25% by weight DPA, about 1 to about 75% by weight LNA, about 0.5 to about 10% by weight arachidonic acid, about 1 to about 80% by weight linoleic acid and about 1 to about 80% by weight CLA.

The fatty acid calcium salts are prepared by adding calcium hydroxide to the fatty acid glyceride-containing feedstock in the range of from about 10 to about 30% by weight of the total composition. A calcium hydroxide level between about 12 and about 18% by weight of the total final calcium salt product composition is preferred.

Additional heat is added to the admixture, if necessary, to increase the temperature to a range between about 150 and about 300° C., and preferably between about 180 and about 250° C. In accordance with the present invention, calcium hydroxide may be substituted by a stoichiometric equivalent of calcium oxide and water, and for purposes of the present invention the term "calcium hydroxide" in the claims is defined as including the replacement in the reactive admixture of calcium hydroxide by a stoichiometric quantity of calcium oxide and water.

The reaction can be performed under vacuum, ambient pressure or at an elevated pressure to maintain the desired temperature. The reaction is performed in an atmospheric environment in which the partial pressure of oxygen is reduced to levels at which a storage-stable saponified calcium salt product will form. Oxygen level reduction may be achieved either by purging a sealed reaction vessel with an inert gas such as nitrogen, carbon dioxide or argon, or by drawing a vacuum. Methods for inert gas purging and vacuum drawing are essentially convention and well known to those skilled in the art. For example, inert gas purging can be accomplished using an inert gas blanket consisting of, for example, nitrogen, carbon dioxide or argon, at a flow rate between about 0.25 to about 50 liters per minute, and preferably between about 1.0 to about 20.0 liters per minute that is applied to the reaction vessel. A vacuum of between about 250 to about 750 mm Hg, and preferably between about 300 to about 500 mm Hg, should be drawn on the sealed vessel, and preferably using an inert gas such as nitrogen, carbon dioxide or argon as the vacuum gas.

Any reduction of the partial pressure of oxygen in the reactive atmosphere will provide an improvement in storage stability. The reduction needed to create a storage-stable product with an adequate shelf life will depend upon the level and degree of unsaturation in the fatty acid glycerides to be saponified, with higher levels and degrees of unsaturation requiring greater reduction in the oxygen content of the reactive atmosphere. Typically the partial pressure of oxygen should be less than about 100 torr, with partial pressures less that 50 torr preferred and partial pressures less that 10 torr even more preferred. The reduction in the partial pressure of oxygen is attained either by displacement of oxygen with the inert gas purge or by drawing a vacuum sufficient to attain a sufficient reduction in total pressure to reduce the partial pressure of oxygen to desired levels.

The amount of time required for the saponification reaction is typically between about 1 to about 15 minutes, and more typically between about 5 and about 10 minutes. The stability of the calcium salts is improved by limiting the reaction time. The reaction is easily identified by the transformation of the admixture into a caramel-like mass. Upon further heating and agitating, the mass further transforms into a taffy-like material, which, upon transfer from the reaction vessel, can easily be processed into free-flowing particles.

The process of the present invention may be employed as either a batch or a continuous process. Examples of reaction vessels suitable for use with the present invention include continuous or batch reactors, indirectly or directly heated, with multiple agitation and shear elements, suitable for very high viscosity materials.

Figure 1:
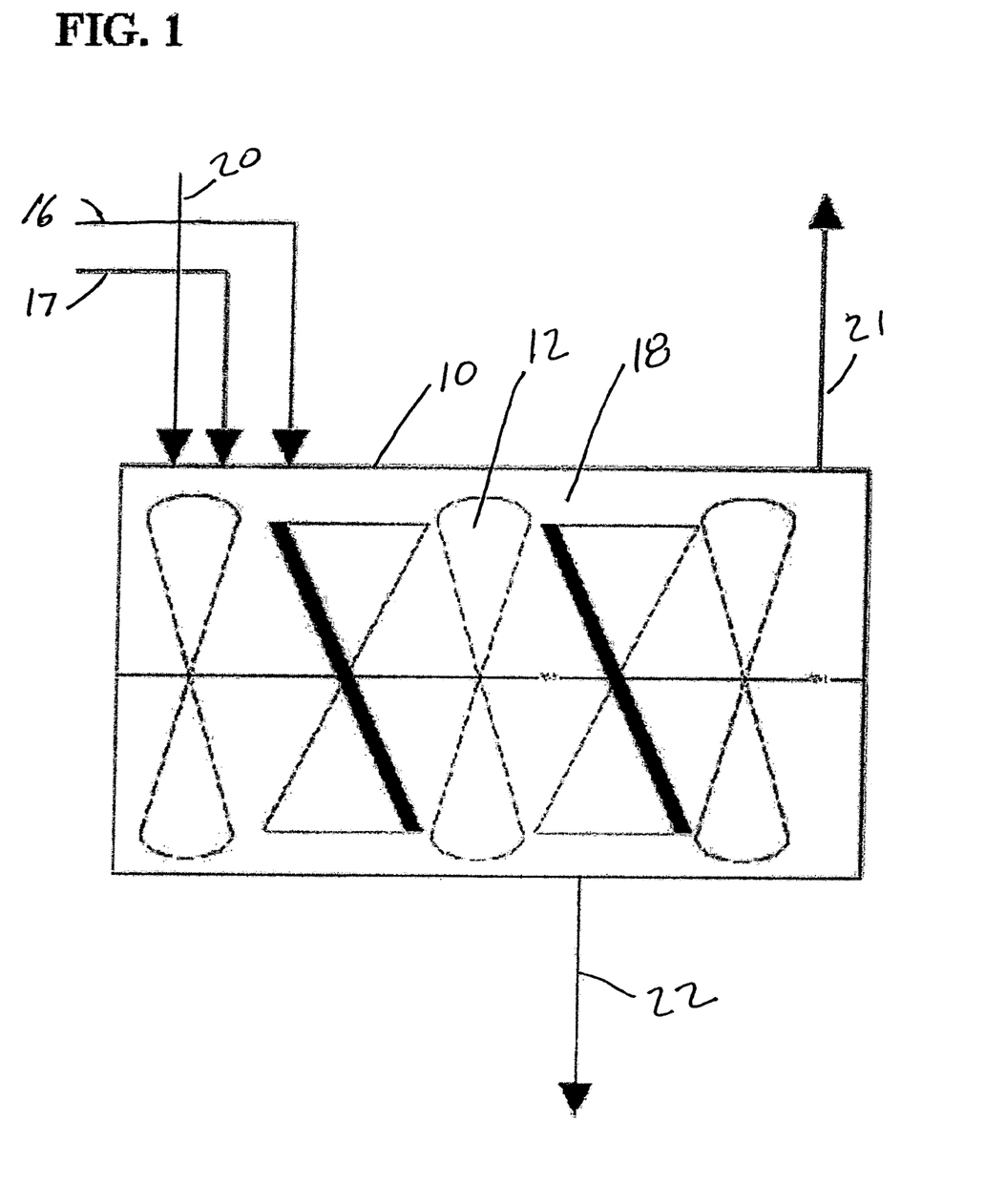
FIG. 1 depicts a batch process according to one embodiment of the present invention.

A batch process according to the present invention is depicted in FIG. 1. Fatty acid glycerides and calcium hydroxide are added via lines 16 and 17, respectively, to the interior 18 of sealed production vessel 10 adapted to supply heat to the vessel contents (not shown), as well as to remove heat therefrom (not shown). The production vessel is equipped with blades 12 for mixing the vessel contents under adequate shear to form a homogenous admixture of the vessel contents.

The production vessel should also be adapted to remove oxygen from the reaction environment, either by forming a vacuum above the vessel contents, or by blanketing the vessel contents with an inert gas such as nitrogen, carbon dioxide or argon. Means by which this can be accomplished are well known to the artisan of ordinary skill. In the embodiment of FIG. 1, line 20 supplies a purge of inert gas to the sealed vessel, in this case nitrogen, which is vented via line 21. Line 21 can be readily be adapted to draw a vacuum as well.

The reaction mixture is heated, reacted and cooled under either the inert gas purge and/or vacuum. After cooling, the mixer blades 12 grind the product into flakes and granules that are discharged from the rector at port 22.

Figure 2:
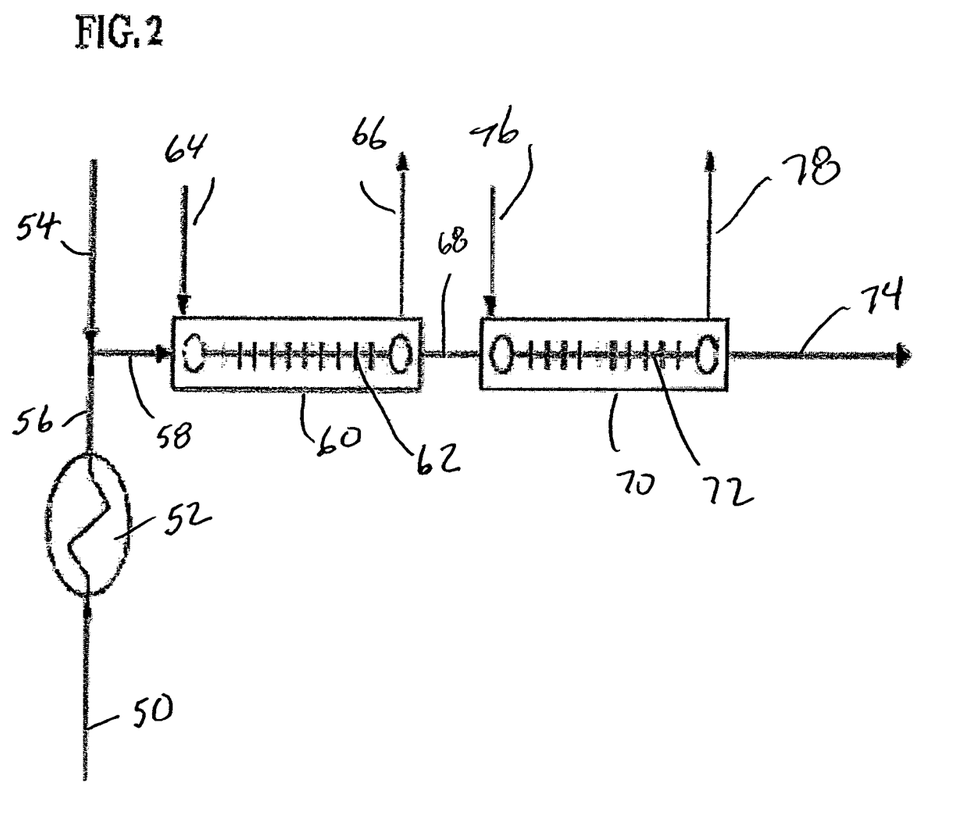
FIG. 2 depicts a continuous process according to another embodiment of the present invention.
Figure 3:
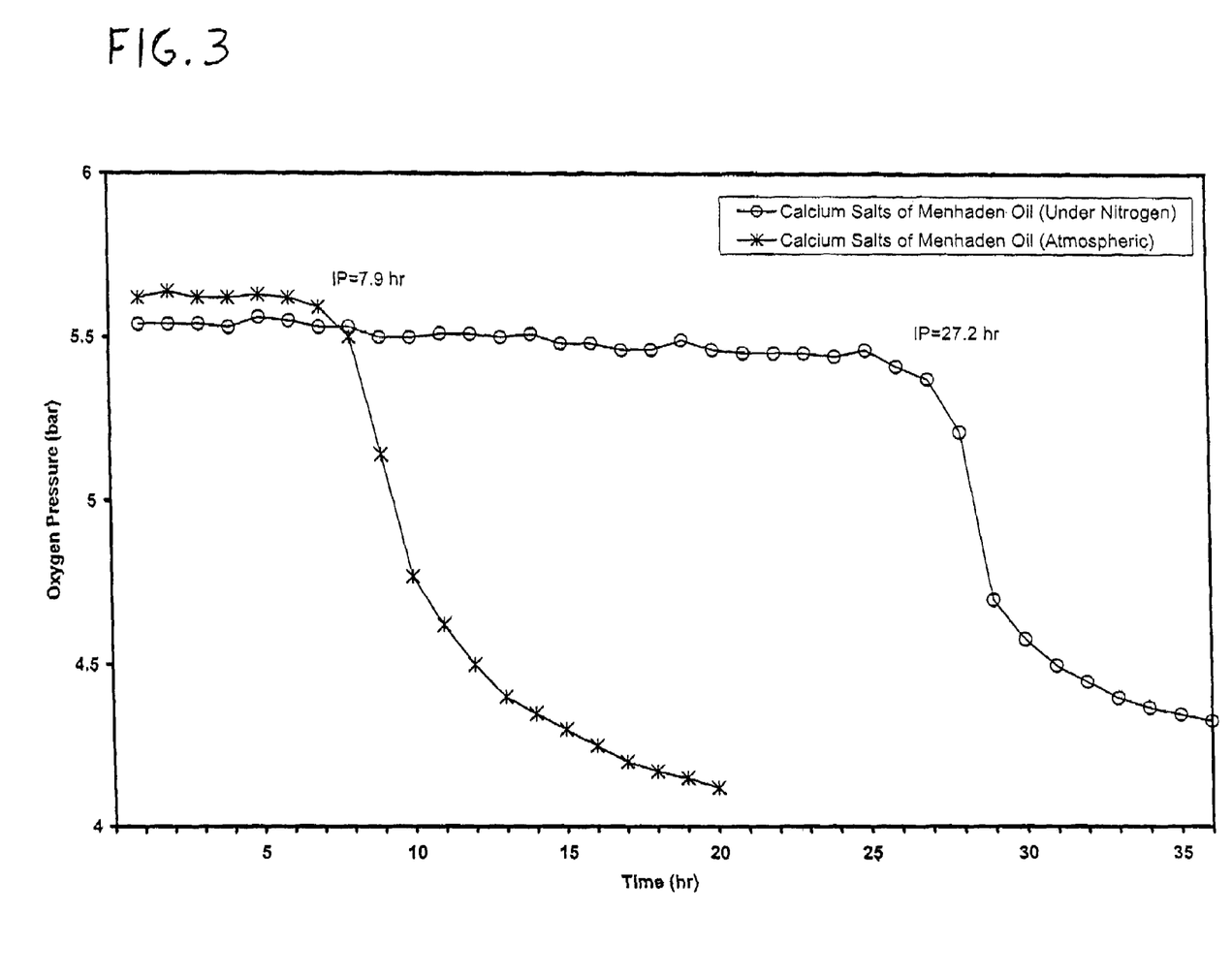
FIG. 3 is an oxidative stability comparison by the Oxipres method of an unsaturated fatty acid calcium salt saponified using nitrogen blanketing according to one embodiment of the present invention, in comparison to a prior art unsaturated fatty acid calcium salt prepared without nitrogen blanketing.

A continuous process according to the present invention is shown in FIG. 2. Feedstock oils are supplied via line 50 to heater 52. Calcium hydroxide is supplied via line 54 and combined with the heated feedstock oil, which is supplied from the heater via line 56. The combination of calcium hydroxide and feedstock oil is then supplied via line 58 to reaction screw conveyor 60, the screw flight 62 of which functions to mix the contents under adequate shear to form a homogenous admixture thereof. The screw conveyor is adapted to supply heat to the reaction mixture (not shown).

Line 64 supplies a purge of inert gas, which in this case is also nitrogen, that exits via vent 66. These lines can also be adapted to draw a vacuum. The product is discharged via line 68 to cooling and grinding screw conveyor 70, the screw flight 72 of which functions to grind the product into flakes and granules that are discharged from screw conveyor 70 at port 74. Screw conveyor 70 is adapted to withdraw heat from the reaction mixture (not shown). Line 76 supplies a purge of inert gas, which is also nitrogen, that exits via vent 78. These lines can also be adapted to draw a vacuum.

The fatty acid calcium salt rumen bypass feed supplements of the present invention may be conveniently fed to a ruminant admixed with a conventional ruminant feed. The feeds are typically vegetable materials edible by ruminants, such as legume hay, grass hay, corn silage, grass silage, legume silage, corn grain, oats, barley, distiller's grain, brewer's grain, soya bean meal and cottonseed meal. Desirably, the amount of the calcium salt supplement in such an admixture does not exceed about 5% of the dry solids content of the feed and is preferably about 2 to about 4% of the dry solids content of the feed. There is no particular lower limit for the amount of the calcium salt to be added to the ruminant feed, although in practice amounts of the calcium salt below about 0.5% of the dry solids content of the feed are too small to provide significant amounts of nutritional supplementation.

While the calcium salts of the present invention can be used as rumen-inert feed supplements for ruminants such as cattle, the calcium salts are also useful in general as nutritional supplements for humans, other mammals, and non-mammals, including birds and fish. Thus, methods in accordance with the present invention add an effective amount of the beneficial unsaturated fatty acid calcium salts of the present invention to a food product including pet food products such as cat food and dog food. Effective amounts include amounts that will provide a food product having a beneficial unsaturated fatty acid content between about 0.05 and about 1.5 weight percent. A beneficial unsaturated fatty acid content between about 0.1 weight percent and about 0.5 weight percent is preferred. Among the beneficial unsaturated fatty acids, polyunsaturated fatty acids, including conjugated polyunsaturated fatty acids, are preferred. This would include non-conjugated omega-3 and omega-6 fatty acids and conjugated fatty acids such as CLA's. Among the omega-3 fatty acids DHA, EPA, DPA and LNA are preferred. Among the omega-6 fatty acids, linoleic acids and arachidonic acids are preferred.

The present invention also includes food products containing the beneficial unsaturated fatty acid calcium salts of the present invention within the ranges described, including pet food products such as cat food and dog food. The cat foods and dog foods include dry, semi-moist and moist cat food and dog food prepared by otherwise conventional methods from conventional formulations incorporating conventional pet food ingredients.

The omega-3 fatty acid calcium salts of the present invention, and particularly those containing one or more omega-3 fatty acids selected from DHA, EPA, DPA and LNA can be used in the fertility enhancement methods disclosed by U.S. Pat. No. 6,576,667, which is incorporated herein by reference. Applicants have since learned that in addition to DHA and EPA, DPA and LNA also enhance the fertility of ruminants and other animals. The present invention makes possible the preparation of fatty acid calcium salts with higher levels of omega-3 fatty acids, thereby reducing the quantities that must be fed to obtain the beneficial effect. The present invention therefore includes methods according to that patent using the omega-3 fatty acid calcium salts of the present invention, including the additionally disclosed omega-3 fatty acid calcium salts not mentioned in that patent.

This should not be interpreted as limiting the scope of the present invention, which provides a means by which beneficial unsaturated fatty acid rich calcium salts may be prepared having utility as nutritional supplements for essentially any animal for which omega-3 fatty acids provide nutritional or therapeutic benefit.

The following non-limiting examples set forth hereinbelow illustrate certain aspects of the invention. All parts and percentages are by weight unless otherwise noted, and all temperatures are in degrees Celsius.

EXAMPLES

Example 1

360 Grams menhaden fish oil was charged to a sealed glass-lined vessel equipped with mixing blades. A 0.5 liter per minute nitrogen blanket was applied to the vessel. The menhaden fish oil was heated to 30° C., and 84 grams calcium hydroxide was added and thoroughly mixed. The vessel was then resealed. The mixture was stirred and heated until the temperature rose to 205° C., at which point the saponification reaction occurred, and the temperature rose to 230° C. During the saponification reaction a light smoke was released and the material formed a yellow taffy-like material. The material was cooled inside the vessel to 25° C., at which point the nitrogen blanket was removed and the vessel was opened. The material, which had hardened through cooling, was discharged from the vessel and processed into small granules of a dry, free-flowing calcium salt.

Example 2

Example 1 was repeated, except that the menhaden fish oil was charged to a sealed glass-lined vessel without nitrogen blanketing. The menhaden fish oil was heated to 25° C., and the calcium hydroxide was added and thoroughly mixed. The vessel was then resealed. A vacuum of 280 nm Hg using nitrogen as the vacuum gas was drawn on the sealed vessel. The mixture was stirred and heated until the temperature rose to 225° C., at which point the saponification reaction occurred, and the temperature rose to 245° C. During the saponification reaction a light smoke was released and the material formed a yellow taffy-like material. The material was cooled inside the vessel to 30° C., at which point the nitrogen blanket was removed and the vessel was opened. The material, which had hardened through cooling, was discharged from the vessel and processed into small granules of a dry, free-flowing calcium salt.

Example 3

One kilogram of menhaden fish oil was charged to a stainless steel vessel equipped with plow mixing and a vacuum stack. A nitrogen blanket having a flow rate of 3.0 liters per minute was applied to the vessel. The menhaden fish oil was heated to 25° C., and 200 grams calcium hydroxide was added and thoroughly mixed using the plow mixers set at between 10 to 20 rpm. The mixture was heated until 205° C., at which point the saponification reaction occurred, and the temperature rose to 212° C. During the saponification reaction a light smoke was released and the material formed a yellow taffy-like material. The material was cooled inside the vessel to 77° C., the plow mixer speed was increased to between 25 to 40 rpm. The material continued to cool inside the vessel and hardened as it cooled. The material was cooled to 38° C., at which point the nitrogen blanket was removed and the vessel was opened. The material was discharged from the vessel and processed into small granules of a dry, free-flowing calcium salt.

Example 4

Example 3 was repeated using 800 grams menhaden fish oil and 160 grams calcium hydroxide.

Example 5

Example 3 was repeated using 21 kilograms menhaden fish oil and 4.2 kilograms calcium hydroxide. The menhaden fish oil was charged to a stainless steel vessel equipped with plow mixing and an internal grinder. A nitrogen blanket having a flow rate of 25 liters per minute was applied to the vessel. The menhaden fish oil was heated to 66° C., and the calcium hydroxide was added and thoroughly mixed using the plow mixers set at between 25 to 40 rpm. During saponification, the temperature rose to 210° C. Upon completion of the saponification reaction, the plow mixer speed was decreased to between 10 to 20 rpm and the internal grinder was turned on. The material continued to cool inside the vessel until 102° C., where the plow mixer speed was increased to between 25 to 40 rpm and the internal grinder was turned off. The material was cooled to 55° C., at which point the nitrogen blanket was removed and the vessel was opened. The material was discharged from the vessel and processed into small granules of a dry, free-flowing calcium salt.

Example 6

Example 5 was repeated using 22 kilograms menhaden fish oil heated to 52° C. and 4.4 kilograms calcium hydroxide. During saponification, the temperature rose to 210° C. The material was cooled inside the vessel to 207° C., the plow mixer speed was decreased to between 10 to 20 rpm and the internal grinder was turned on. The material continued to cool inside the vessel until 163° C., where the plow mixer speed was increased to between 25 to 40 rpm and the internal grinder was turned off. The material was cooled to 55° C., at which point the nitrogen blanket was removed and the vessel was opened. The material was discharged from the vessel and processed into small granules of a dry, free-flowing calcium salt.

Example 7

In a continuous process using the nitrogen blanketed equipment of FIG. 2, menhaden fish oil was preheated to 230° C., then metered into the unit with calcium hydroxide added at the rate of 20% by weight of the oil by a weight loss meter. The temperature of the mixture increased in the unit up to 250° C. at the point of discharge. The material was cooled and milled into a granular free flowing calcium salt. During a six-hour continuous production run 450 lbs of calcium salt was produced.

Example 8

In a batch process, 40 lbs menhaden fish oil and 7 lbs calcium hydroxide was added to the nitrogen blanketed unit of FIG. 1. The vessel was operated at a temperature of 220° C. When the material formed a thick liquid it was discharged by gravity flow though a ball valve onto a cooling tray. The material crystallized on the tray in thirty minutes after which it was pooled and then milled in into granular free flowing calcium salts.

Example 9

One kilogram soy acid oil was charged to a stainless steel vessel equipped with plow mixing, and heated to 196° C. with the nitrogen blanketing flow rate set as in Example 3. 200 grams calcium hydroxide was added and thoroughly mixed using the plow mixers set at between 10 to 20 rpm. The mixture was heated until 202° C., at which point the saponification reaction occurred, and the temperature rose to 207° C. During the saponification reaction a light smoke was released and the material formed a grey taffy-like material. The material was discharged from the reactor by gravity. The material hardened as it cooled and was processed into small granules of a dry, free-flowing calcium salt.

In the following examples, calcium salt product stability is measured by the Oxipres method. The Oxipres method is a modification of the ASTM oxygen bomb method. Unlike the oxygen bomb method there is no traditional oil bath heat transfer medium and a pressure transducer is used instead of a circular pressure recorder. The oxygen bomb method for oxidative stability is an accelerated oxidation model. It uses elevated temperatures and pure oxygen at elevated pressures to model the oxidative stability of fats and oils.

The measured material is charged into a glass chamber which is loaded in a stainless steel oxygen "bomb" vessel. A known quantity of pure oxygen, in these cases 5 bar is added to the vessel, and the vessel is sealed. The sealed vessels are placed in an oven at a constant temperature, in the present examples 60° C. and 80° C. A pressure transducer measures the level of oxygen remaining in the vessel. The consumption of oxygen is determined by the pressure drop in the bomb during the experiment. Oxygen is consumed as oxidation occurs. The output from the pressure transducers are sent to a computer which graphs the time-pressure relationship and saves a data point once every 60 seconds.

The output graphs display two characteristics. The first is the induction period, which is defined as the time from time zero until the point at which a drastic change in the slope of the oxidative deterioration graphs occurs. The second is the rate of oxidation, which corresponds to the slope of the oxidative deterioration graph immediately after the induction period when oxidation is taking place. These two characteristics are used to compare the relative oxidative stability of materials to each other under like conditions.

Comparative Example

No Nitrogen Blanketing or Vacuum

Example 3 was repeated without nitrogen blanketing and with heating of the menhaden fish oil to 38° C. The mixture was heated until 207° C., at which point the saponification reaction occurred, and the temperature rose to 215° C. The material was discharged from the reactor by gravity. The material hardened as it cooled and was processed into small granules of a dry, free-flowing calcium salt.

Example 10

Example 5 was repeated using 22 kilograms menhaden fish oil heated to 55° C. and 4.4 kilograms calcium hydroxide. The mixture was heated as in example 9. During the saponification reaction a light smoke was released and the material formed a yellow taffy-like material. At this point the nitrogen blanket was removed and the material was discharged by gravity through a valve on the bottom. The material was cooled and rolled into a 2-inch layer. When the material hardened and cooled below 65° C. it was processed into small granules of a dry, free-flowing calcium salt.

Figure 4:
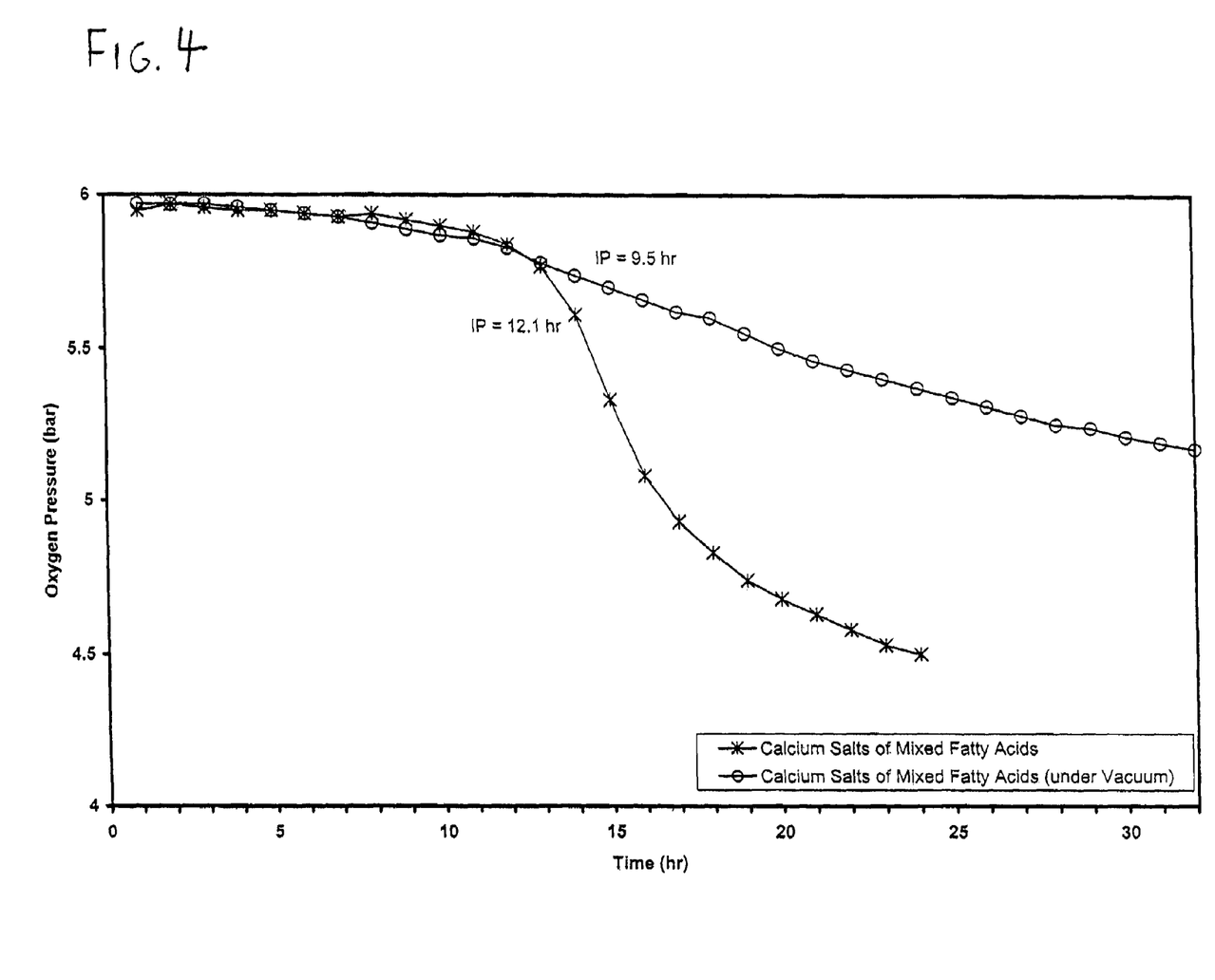
FIG. 4 is an oxidative stability comparison by the Oxipres method of an unsaturated fatty acid calcium salt saponified under vacuum according to one embodiment of the present invention, in comparison to a prior art unsaturated fatty acid calcium salt prepared under an ambient atmosphere.

FIG. 4 compares the oxidative stability measured by the Oxipres method of the saponified calcium salts of the Comparative Example with the saponified calcium salts of Example 10 at 60° C. The graph shows that the sample of calcium salts that was processed under a nitrogen blanket showed greater resistance to oxidation than the sample processed under atmospheric conditions. The induction period of the calcium salt produced under nitrogen was 27.2 hrs while the induction period of the calcium salt processed in atmospheric conditions was 7.9 hrs. The induction period is the relative resistance to the start of oxidation.

Example 11

The calcium salts of the Comparative Example and Example 2 were each blended in a 20:80 weight ratio with neutralized calcium salts of vegetable fatty acids (Palm Fatty Acid Distillates). FIG. 5 depicts a comparison of the oxidative stability of the two samples measured by the Oxipres method at 80° C. The graph shows that the induction period of both calcium salts are similar meaning the resistance to initial oxidation is similar for each sample. The calcium salt processed in a vacuum shows a curve with an oxidation slope reflecting that it has a slower rate of oxidation after initial oxidation begins than the sample processed in atmospheric conditions.

The foregoing examples thus demonstrate the saponification method of the present invention and the storage stability advantages obtained therefrom. The foregoing examples and description of the preferred embodiment should be taken as illustrating, rather than as limiting, the present invention as defined by the claims. Numerous variations and combinations of the features set forth above can be utilized without departing from the present invention as set forth in the claims and all such modifications are intended to be included within the scope of the following claims.

What is claimed is:

1. A method for the preparation of a storage-stable fatty acid calcium salt product comprising:
   forming a reactive admixture comprising (a) an unsaturated fatty acid glyceride feedstock; and (b) from about 10% to about 30% of the total admixture weight of calcium hydroxide; and
   heating the admixture to a temperature at which said fatty acid glycerides saponify to form fatty acid calcium salts in an atmosphere in which the partial pressure of oxygen has been reduced by an amount effective to provide an improvement in storage stability.

2. The method of claim 1, wherein said partial pressure of oxygen is reduced by inert gas blanketing of said admixture while heating.

3. The method of claim 2, wherein said inert gas comprises nitrogen.

4. The method of claim 1, wherein said partial pressure of oxygen is reduced by heating said admixture under vacuum.

5. The method of claim 1, wherein said unsaturated fatty acid glyceride feedstock comprises an unsaturated fatty acid concentration sufficient to form unstable calcium salt products when saponified in an ambient atmosphere.

6. The method of claim 1, wherein said unsaturated fatty acid glyceride feedstock comprises polyunsaturated fatty acids.

7. The method of claim 6, wherein said polyunsaturated fatty acids are selected from the group consisting of omega-3 and omega-6 fatty acids and combinations of either or both.

8. The method of claim 7, wherein said polyunsaturated fatty acids comprise one or more omega-3 fatty acids selected from the group consisting of DHA, EPA, DPA and LNA.

9. The method of claim 6, wherein said polyunsaturated fatty acids comprise one or more conjugated fatty acids.

10. The method of claim 9, wherein said one or more conjugated fatty acids comprise one or more CLA isomers.

11. The method of claim 1, wherein said fatty acid glyceride feedstock comprises a mixture of two or more C10–C22 fatty acids having greater than about 45% by weight of the fatty acid content in the form of fatty acid glycerides.

12. The method of claim 11, wherein about 85 and about 100% by weight of said fatty acid mixture is in the form of fatty acid glycerides.

13. The method of claim 1, wherein said fatty acid glyceride feedstock comprises from about 40 to about 95% by weight of unsaturated fatty acids.

14. The method of claim 1, wherein said feedstock comprises up to about 100% by weight of fish oil.

15. The method of claim 14, wherein said fish oil is selected from the group consisting of menhaden, herring, mackerel, caplin, tilapia, tuna, sardine, pacific saury and krill oils.

16. The method of claim 15, wherein said fish oil comprises one or more omega-3 or omega-6 fatty acids selected from the group consisting of DHA, EPA, DPA, LNA, linoleic acid and arachidonic acid.

17. The method of claim 1, further comprising the step of cooling said admixture and forming a solid, free-flowing and granular fatty acid calcium salt product.

18. The method of claim 17, wherein said admixture is cooled in said atmosphere in which said partial pressure of oxygen has been reduced by an amount effective to provide an improvement in storage stability.

19. A fatty acid calcium salt prepared by the method of claim 1, wherein said unsaturated fatty acid glyceride feedstock comprises from about 40 to about 95% by weight of unsaturated fatty acids, with greater than 45% by weight being in the form of fatty acid glycerides; and wherein said calcium salt comprises one or more beneficial unsaturated fatty acids.

20. A fatty acid calcium salt according to claim 19, comprising polyunsaturated fatty acids.

21. The fatty acid calcium salt of claim 20, wherein said polyunsaturated fatty acids are selected from the group consisting of omega-3 and omega-6 fatty acids and combinations of either or both.

22. The fatty acid calcium salt of claim 21, wherein said polyunsaturated fatty acids comprise one or more omega-3 or omega-6 fatty acids selected from the group consisting of DHA, EPA, DPA, LNA, linoleic acid and arachidonic acid.

23. The fatty acid calcium salt of claim 22, comprising at least one polyunsaturated fatty acid selected from the group consisting of about 1 to about 25% by weight DHA, about 1 to about 25% by weight EPA, about 1 to about 25% by weight DPA, about 1 to about 75% by weight LNA, about 0.5 to about 10% by weight arachidonic acid, about 1 to about 80% by weight linoleic acid and about 1 to about 80% by weight CLA.

24. The fatty acid calcium salt of claim 20, wherein said polyunsaturated fatty acids comprise one or more conjugated fatty acids.

25. The fatty acid calcium salt of claim 24, wherein said one or more conjugated fatty acids comprise one or more CLA isomers.

26. A fatty acid calcium salt prepared by the method of claim 12, wherein said fatty acid glyceride feedstock comprises from about 40 to about 95% by weight of unsaturated fatty acids.

27. A fatty acid calcium salt prepared by the method of claim 13.

28. A fatty acid calcium salt prepared by the method of claim 14, wherein said fatty acid glyceride feedstock comprises from about 40 to about 95% by weight of unsaturated fatty acids.

29. The fatty acid calcium salt of claim 28, wherein said fish oil is selected from the group consisting of menhaden, herring, mackerel, caplin, tilapia, tuna, sardine, pacific saury and krill oils.

30. The fatty acid calcium salt of claim 29, wherein said fish oil comprises one or more omega-3 or omega-6 fatty acids selected from the group consisting of DHA, EPA, DPA, LNA, linoleic acid and arachidonic acid.

31. A rumen bypass feed supplement comprising the fatty acid calcium salt of claim 19, 20, 21, 22, 23, 24, 25, 26, 27, 28, 29 or 30.

32. A storage-stable calcium salt saponification product of an unsaturated oil consisting essentially of one or more fish oils, wherein said one or more fish oils comprise from about 40 to about 95% by weight of unsaturated fatty acids, with greater than 45% by weight being in the form of fatty acid glycerides.

33. The saponification product of claim 32, wherein said one or more fish oils are selected from the group consisting of menhaden, herring, mackerel, caplin, tilapia, tuna, sardine, pacific saury and krill oils.

34. The saponification product of claim 32, wherein said one or more fish oils comprise one or more fatty acids selected from the group consisting of omega-3 and omega-6 fatty acids.

35. The saponification product of claim 34, wherein said one or more fish oils comprise one or more omega-3 or omega-6 fatty acids selected from the group consisting of DHA, EPA, DPA, LNA, linoleic acid and arachidonic acid.

36. The saponification product of claim 35, comprising at least one polyunsaturated fatty acid selected from the group consisting of about 1 to about 25% by weight DHA, about 1 to about 25% by weight EPA, about 1 to about 25% by weight DPA, about 1 to about 75% by weight LNA, about 0.5 to about 10% by weight arachidonic acid, about 1 to about 80% by weight linoleic acid and about 1 to about 80% by weight CLA.

37. A rumen bypass feed supplement comprising the saponification product of claim 32.

38. A storage-stable fatty acid calcium salt saponification product of a fatty acid glyceride feedstock having an unsaturated fatty acid concentration sufficient to form unstable calcium salt products when saponified in an ambient atmosphere, wherein said fatty acid glyceride feedstock comprises from about 40 to about 95% by weight of unsaturated fatty acids, with greater than 45% by weight being in the form of fatty acid glycerides.

39. The fatty acid calcium salt of claim 38, wherein said unsaturated fatty acid glyceride feedstock comprises polyunsaturated fatty acids.

40. The fatty acid calcium salt of claim 39, wherein said polyunsaturated fatty acids are selected from the group consisting of omega-3 and omega-6 fatty acids and combinations of either or both.

41. The fatty acid calcium salt of claim 40, wherein said polyunsaturated fatty acids comprise one or more omega-3 or omega-6 fatty acids selected from the group consisting of DHA, EPA, DPA, LNA, linoleic acid and arachidonic acid.

42. The fatty acid calcium salt of claim 41, comprising at least one polyunsaturated fatty acid selected from the group consisting of about 1 to about 25% by weight DHA, about 1 to about 25% by weight EPA, about 1 to about 25% by weight DPA, about 1 to about 75% by weight LNA, about 0.5 to about 10% by weight arachidonic acid, about 1 to about 80% by weight linoleic acid and about 1 to about 80% by weight CLA.

43. The fatty acid calcium salt of claim 39, wherein said polyunsaturated fatty acids comprise one or more conjugated fatty acids.

44. The fatty acid calcium salt claim 43, wherein said one or more conjugated fatty acids comprise one or more CLA isomers.

45. The fatty acid calcium salt of claim 38, wherein said fatty acid glyceride feedstock comprises from about 50 to about 85% by weight of unsaturated fatty acids.

46. A rumen bypass feed supplement comprising the fatty acid calcium salt of claim 38, 39, 40, 41, 42, 43 or 44.

* * * * *